United States Patent [19]

Buhs et al.

[11] 4,333,925

[45] Jun. 8, 1982

[54] DERIVATIVES OF C-076 COMPOUNDS

[75] Inventors: Rudolf P. Buhs, Short Hills; Theodore A. Jacob, Westfield; Gerald Miwa, Maplewood; Elena Sestokas, Rahway; Rae Taub, Metuchen; John S. Walsh, Avenel, all of N.J.

[73] Assignee: Merck & Co., Inc., Rahway, N.J.

[21] Appl. No.: 262,082

[22] Filed: May 11, 1981

[51] Int. Cl.$^3$ ...................... A61K 31/71; C07H 17/08
[52] U.S. Cl. .................................. 424/181; 424/180; 536/7.1
[58] Field of Search ................ 260/343.41; 536/17 R, 536/4; 424/180, 181

[56] References Cited

U.S. PATENT DOCUMENTS

| 4,199,569 | 4/1980 | Chabala et al. | 424/180 |
| 4,285,963 | 8/1981 | Areson et al. | 260/343.41 |
| 4,289,760 | 9/1981 | Mrozik et al. | 260/343.41 |

FOREIGN PATENT DOCUMENTS 1573955  8/1980  United Kingdom.

*Primary Examiner*—Blondel Hazel
*Attorney, Agent, or Firm*—David L. Rose; Mario A. Monaco

[57] ABSTRACT

There are disclosed certain new derivatives of C-076 compounds which have been isolated from the livers of animals that had been administered ivermectin and the in vitro incubation of such compounds with animal liver preparations. The compounds retain the basic ivermectin structure, however, 24-methyl group has been oxidized to a hydroxy methyl group and, in some of the new compounds the disaccharide substituent of the starting materials has been cleaved to a monosaccharide moiety. The new compounds have been found to retain the biological activity of the parent C-076 compounds. The compounds are thus potent antiparasitic agents and compositions and methods for such uses are also disclosed.

8 Claims, No Drawings

DERIVATIVES OF C-076 COMPOUNDS

BACKGROUND OF THE INVENTION

The C-076 family of compounds are a series of macrolides isolated from the fermentation broth of a strain of *Streptomyces avermitilis*. The C-076 compounds are characterized by having a 16-membered cyclic backbone substituted with a disaccharide and having a bicyclic spiroketal fused thereon. The compounds have the structure:

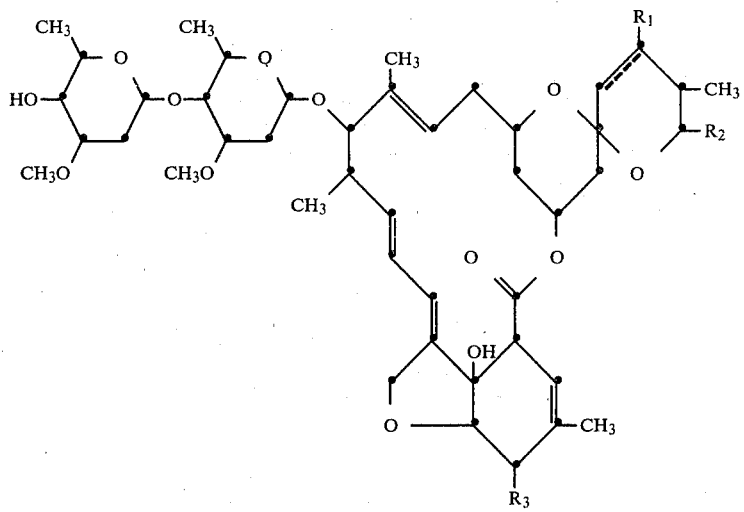

wherein
the broken line indicates a single or a double bond;
$R_1$ is hydroxy and is present only when said broken line indicates a single bond;
$R_2$ is iso-propyl or sec-butyl; and
$R_3$ is methoxy or hydroxy.

The C-076 compounds are named using a system of designations which corresponds to the structural variations as is set forth in the following table.

| Compound | $R_1$ | $R_2$ | $R_3$ |
|---|---|---|---|
| A1a | Double bond | sec-butyl | —OCH$_3$ |
| A1b | Double bond | iso-propyl | —OCH$_3$ |
| A2a | —OH | sec-butyl | —OCH$_3$ |
| A2b | —OH | iso-propyl | —OCH$_3$ |
| B1a | Double bond | sec-butyl | —OH |
| B1b | Double bond | iso-propyl | —OH |
| B2a | —OH | sec-butyl | —OH |
| B2b | —OH | iso-propyl | —OH |

The above compounds are isolated from the fermentation broth of *Streptomyces avermitilis* using normal extraction and isolation procedures. The C-076 producing culture and the morphological characteristics thereof along with the procedures used for separating and isolating the C-076 compounds, are fully described in Great Britain Pat. No. 1573955.

The fermentation is carried out in an aqueous medium and includes an assimilable source of carbon, an assimilable source of nitrogen and inorganic salts and the fermentation is generally carried out under aerobic conditions. The specific nutrients and parameters for the fermentation are described completely in the above cited Great Britain patent.

The C-076 producing culture and a mutant thereof have been deposited in the permanent culture collection of the American Type Culture Collection, 12301 Parklawn Drive, Rockville, Md. 20852. The cultures are accessible under the accession numbers ATCC 31267 for the basic culture and ATCC 31272 (lyophilized tube) and ATCC 31271 (frozen vial) for the mutant. The C-076 compounds are potent antiparasitic agents with very broad spectrum anthelmintic, acaricidal, nematocidal and insecticidal activity.

Derivatives of the C-076 compounds have been prepared which also have considerable antiparasitic activity. In particular a mixture of at least 80% of 22,23-dihydro C-076 B1a and no more than 20% of 22,23-dihydro C-076 B1b is particularly effective and such a mixture has been given the generic name of ivermectin. Such compounds are disclosed in U.S. Pat. No. 4,199,569.

SUMMARY OF THE INVENTION

The instant invention is concerned with novel C-076 derivatives and procedures for their preparation. Thus, it is an object of this invention to describe such novel C-076 derivatives. It is a further object of this invention to describe the processes for their preparation by oxidation with liver microsomal preparations and by isolation from the livers of animals that had been given ivermectin. A still further object is to describe the antiparasitic effects of such novel compounds. Further objects will become apparent from a reading of the following description.

DESCRIPTION OF THE INVENTION

The novel compounds of this invention are best described in the following structural formula:

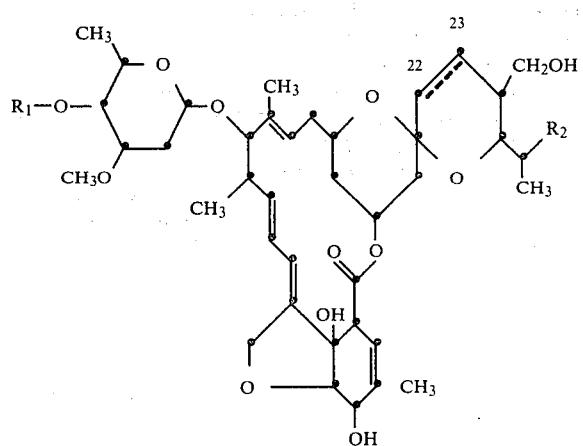

wherein $R_1$, $R_2$ and the 22,23 broken line have the following meanings:

| Compound | $R_1$ | $R_2$ | 22,23-bond |
|---|---|---|---|
| I | CH₃ with HO—, CH₃O— substituted pyran | —CH₂CH₃ | double bond |
| II | —H | —CH₂CH₃ | single bond |
| III | CH₃ with HO—, CH₃O— substituted pyran | —CH₂CH₃ | single bond |
| IV | —H | —CH₃ | single bond |
| V | CH₃ with HO—, CH₃O— substituted pyran | —CH₃ | single bond |

The compounds of this invention are prepared by either of two methods. The first is the in vitro incubation of ivermectin in rat or steer liver microsomes. The second is the in vivo method of extraction of the liver of animals, primarily rats, sheep or cattle, that had been administered a C-076 compound (substrate).

In Vitro Method.

The rat or steer liver microsomes are prepared using standard techniques for doing so wherein livers from such animals are homogenized in a buffer solution and subjected to fractional centrifugation. The initial centrifugation at about 20,000 xg or less removes the bulk of the solid material having the microsomes suspended in the buffer solution. Recentrifugation of the supernatant at higher rotations of about 100,000 xg or higher results in a pellet of liver microsomes.

The substrate is then incubated with the liver microsomes at a rate of about one mg of ivermectin with from 10 to 100 mg of liver microsomal protein. Preferably for each mg of substrate about 20 mg of liver microsomal protein is employed. The incubation is carried out in a mixture of solvents, preferably employing a lower alcohol such as methanol or ethanol, and an aqueous buffer solution. The buffering salts used in the microsomal incubation system are generally standard buffers known to those skilled in the art. Examples of such are alkali metal phosphates, preferably potassium phosphate.

Also present in the microsomal incubation system is an NADPH-generating system such as NADP, glucose-6-phosphate dehydrogenese, and glucose-6-phosphate. These agents provide cofactors for the liver microsomes and provide an enzyme system such as would be found in an in vivo situation. While all three of the foregoing are needed to properly generate NADPH, those skilled in the art will appreciate that other similar agents may be substituted for one or more of the listed agents while still retaining NADPH generating properties. NADP is generally used at a rate of from about 0.05 to 5 micromoles ($\mu$M) for each mg of liver microsomal protein. Preferably about 0.25 $\mu$M of NADP is employed for each mg of liver microsomal protein. The glucose-6-phosphate dehydrogenese is generally employed at from about 0.5 to 10 units for each 10 mg of liver microsomal protein. Preferably about 1 to 2 units of glucose-6-phosphate-dehydrogenese is employed for each 10 mg of liver microsomal protein. Additionally from about 0.5 to 50 $\mu$M, preferably about 2.5 $\mu$M of glucose-6-phosphate is added to the microsomal incubation mixture for each mg of liver microsomal protein in order to adequately provide a source of NADPH.

The incubation is carried out generally in two stages over a period of from ½ to 4 hours. Approximately one half of the liver microsomal protein are added to the remainder of the materials and incubated for about 15 minutes to 2 hours. Then the remainder of the liver microsomal protein are added and incubated for an equal period of time. The incubation is carried out aerobically and with vigorous stirring or shaking. The incubation is carried out at from about 25° to 40° C. The preferred incubation temperature is about 37° C.

At the end of the incubation period the reaction is stopped by the addition of a water miscible organic solvent, such as acetone to precipitate the protein which may be removed by filtration if desired. The novel compounds thus produced are isolated and purified using solvent extraction and chromatography techniques. In particular, high performance liquid chromatography (HPLC) has been found to be especially useful for the isolation of the instant compounds.

The compounds of this invention are also isolated in an in vivo preparation by extracting the livers of animals, preferably sheep or cattle, that had been administered ivermectin. The animals are generally administered from 10 to 500 $\mu$g/kg of animal body weight. The liver is excised and homogenized in a mixture of water and an organic solvent, preferably acetone, and filtered. Using extraction techniques followed by sequential HPLC treatments, purified metabolite fractions containing the compound of this invention are obtained.

The novel compounds of this invention have significant parasiticidal activity as anthelmintics, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The C-076 compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

The instant compounds are also useful against parasites which infect humans. The most common genera of parasites of the gastro-intestinal tract of parasites of man are Ancylostoma, Necator, Ascaris, Strongyloides, Trichinella, Capillaria, Trichuris, and Enterobius. Other medically important genera of parasites which are found in the blood or other tissues and organs outside the gastro-intestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly Musca domestica.

The compounds are also useful against insect pests of stored grains such as Tribolium sp., Tenebrio sp. and of agricultural plants such as spider mites, (Tetranychus sp.), aphids, (Acyrthiosiphon migratory orthopterans such as locusts and immature stages of insects living on plant tissue. The compounds are useful as a nematocide for the control of soil nematodes and plant parasites such as Meloidogyne spp. which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or dicalcium phosphate.

Where it is desired to administer the C-076 compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol, formal and aqueous parenteral formulations are also used. The active C-076 compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally, good results are obtained with our novel compounds by the oral administration of from about 0.001 to 10 mg. per kg. of animal body weight, such total dose being given at one time or in divided doses over a relatively short period of time such as 1-5 days. With the preferred compounds of the invention, excellent control of such parasites is obtained in animals by administering from about 0.025 to 0.5 mg. per kg. of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active C-076 compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular C-076 compound employed, the compounds of this invention are usually fed at concentrations of between 0.00001 to 0.002% in the feed in order to achieve the desired antiparasitic result.

In using the compounds of this invention, the individual C-076 components may be isolated and purified and used in that form. Alternatively, mixtures of the individual C-076 components may be used. It is not necessary to completely separate the various C-076 compounds obtained from the purification of the microsomal incubation or liver extraction.

The C-076 compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples describe the isolation and purification procedures for the preparation of the instant compounds. The examples are provided in order that the invention might be more fully understood. They should not be construed as limitative of the invention.

EXAMPLE 1

METHODS:

A. Preparation of Liver Microsomes

Microsomes from either steer or rat livers are prepared by homogenizing freshly obtained liver samples (10 g) with 0.05 M Tris, pH 7.5, containing 1.15% KCl (30 ml). The samples are centrifuged for 20 min. at $10,000 \times g$ and the supernatant recentrifuged for 60 min. at $105,000 \times g$. The resulting microsomal pellet is washed by resuspending it in 1.15% KCl containing 10 mM EDTA. Centrifugation for 60 min. at $105,000 \times g$ gives a washed microsomal pellet which was resuspended in 0.25 M sucrose and stored at $-80°$ C. at a protein concentration of approximately 30–40 mg/ml.

B. Substrate

In a typical preparative incubation, an alcohol solution of 10 ml containing 10 mg of 22,23-dihydro C-076 B1a is placed in a 500 ml Erlenmeyer flask and the alcohol solvent removed under a stream of nitrogen. The substrate residue is then redissolved in 0.5 ml methanol and the following added (a) microsomes from either steer or rat livers equivalent to 200 mg protein, (b) 10 ml of 1 M potassium phosphate buffer, pH 7.4, (c) 10 ml of 10 mM NADP, (d) 20 ml of 0.05 M glucose-6-phosphate, (e) 5 ml of 14 units/ml glucose-6-phosphate dehydrogenase and (f) water to bring the total volume to 90 ml.

C. Incubation

The sample is aerobically incubated with shaking at 37° C. for 30 min, after which another addition of microsomes (200 mg in 40 ml 0.01 M potassium phosphate buffer, pH 7.4) is made and the sample incubated an additional 30 min. The reaction is stopped and the protein precipitated by the addition of 100 ml of acetone.

D. Sample Cleanup by Solvent Extraction

The samples are partially purified by solvent extraction. The quenched samples are extracted with methylene chloride ($3 \times 200$ ml) and the organic extract evaporated to dryness on a rotary evaporator. The residue is dissolved in three successive 33 ml volumes of ethanol/0.1 M $K_2PO_4$, pH 7.0 (40/60). This aqueous solution is extracted with cyclohexane ($3 \times 60$ ml) to remove the unmetabolized substrate. The aqueous solution is then extracted with methylene chloride ($2 \times 100$ ml and $1 \times 50$ ml) to recover the metabolites. The methylene chloride is removed by rotary evaporation and the metabolite residue redissolved in 5 ml methylene chloride. The polar metabolites in this solution are adsorbed onto a Silica Gel Sep Pak (Waters Assoc., Milford, Mass.) and eluted with ethyl acetate. The ethyl acetate eluate is evaporated to dryness and the residue dissolved in a small volume (200 $\mu$l) of methanol. Any insoluble material is removed by centrifugation.

E. HPLC Purification of Metabolites

The entire sample (200 $\mu$l) is injected onto a 4.6 mm inside diameter $\times 25$ cm Zorbax ODS column (Dupont Co., Wilmington, Del.) and isocratically eluted with acetonitrile/methanol/water (39/26/35) for 25–30 min at a flow rate of 1.6 ml/min. A 15 min linear gradient to 100% acetonitrile/methanol (60/40) is then used to remove any less polar materials including residual substrate. The U.V. profile at 245 nm was continuously monitored while fractions equivalent to 1 min (1.6 ml) were collected and 100 $\mu$l aliquots taken for countings. Under these conditions, two fractions containing polar metabolites (identified as peaks I and II) eluted in fractions 5–8 and 10–12 corresponding to retention times of approximately 7 and 11 mins, respectively.

The fractions containing the more polar metabolite (peak I) are pooled, 3 ml of water added and the metabolite extracted into methylene chloride ($2 \times 3$ ml). The organic extract is evaporated to dryness under a stream of nitrogen and the residue dissolved in about 100 $\mu$l of methanol. The sample is then injected onto the same Zorbax column and eluted isocratically for 30 min with acetonitrile/methanol/water (36/24/40) before initiating the acetonitrile/methanol gradient (60/40). This HPLC purification procedure is repeated, as necessary until a single, symmetrical peak is eluted from the column as assessed by UV absorbance. This is Compound II (11.8 $\mu$g).

Samples of the later eluting metabolite corresponding to peak II are also purified by HPLC. The fractions rich in peak II from the first HPLC are pooled, extracted into methylene chloride and purified by HPLC in a manner identical to that used for peak II affording Compound III (60–80 μg).

EXAMPLE 2

The procedure of Example 1 is followed using 10 mg of 22,23-dihydro C-076 Blb in place of 22,23-dihydro C-076 bla and then in recovered Compound IV (11.8 μg) and Compound V (63.7 μg).

EXAMPLE 3

The procedure of Example 1 is followed using 10 mg of C-076 Bla and Compound I (10.4 μg) is obtained.

EXAMPLE 4

I. Isolation Procedure

Two 500 g liver samples from 14-day post-dose steers have been administered 0.3 mg/kg of ivermectin, were extracted by the following procedure:
1. Five portions of 100 g liver, 200 ml of water, and 300 ml of acetone are homogenized in a blender.
2. The homogenate is filtered through a sintered glass funnel packed with a layer of supercel. The residue is washed with 1260 ml of acetone/water (1/1).
3. The filtrate and washes are then extracted with about 1500 ml of methylene chloride. The methylene chloride extract is evaporated, and the residue dissolved in 102 ml of absolute alcohol.
4. To the alcohol solution is added 150 ml of 0.1 M, pH 7 phosphate buffer and extracted with 150 ml of cyclohexane. The cyclohexane layer is removed.
5. The ethanol/buffer layer is re-extracted with 300 ml of methylene chloride. The methylene chloride layer is removed and evaporated. The residue is dissolved in 10 ml of methanol and transferred to a 15 ml centrifuge tube.
6. The methanol solution is evaporated to dryness, the residue dissolved in 1 ml of isooctane/ethanol (75/25), and centrifuged. The supernatant is subjected to HPLC purification.

II. Purification by HPLC

The final extract from each 500 g tissue sample is chromatographed four times before the two partially purified metabolites are combined and rechromatographed as described in II.4.
1. The first chromatography on the final liver extract is an adsorption chromatography through a silica gel column with isooctane/ethanol (75/25) as the solvent system.
2. Thereafter, five HPLC chromatographies (No. 2–6) are completed using the reversed-phase conditions with a Zorbax ODS column and acetonitrile/methanol/water (36/24/40) as the solvent system.
3. Peak fractions from each chromatography are sequentially pooled and extracted with methylene chloride. The extract is evaporated, and the residue dissolved in 0.1 ml of methanol and centrifuged in preparation for HPLC injection.
4. The peak fractions from the 4th HPLC of each sample are combined and the extract is evaporated, and the residue dissolved in Methanol for the 5th and 6th chromatographies using similar conditions as in No. 2.
5. The final peak fractions from the 6th HPLC are combined and evaporated to dryness.

This sample weighing 8.5 μg is identified using nuclear magnetic resonance and mass spectrometry, as Compound III.

What is claimed is:

1. A compound having the formula:

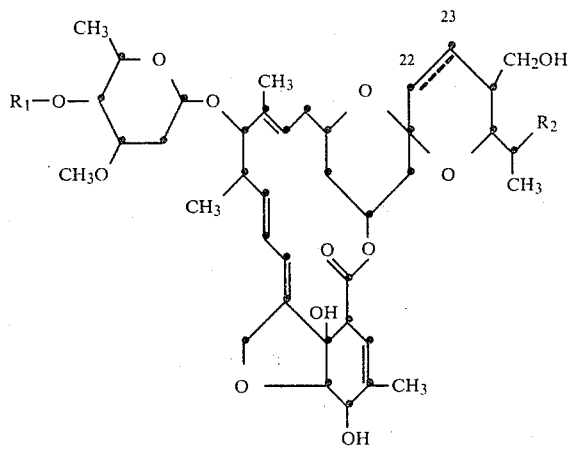

wherein $R_1$, $R_2$ and the 22, 23 broken line have the following meanings:

In Compound I, $R_1$ is

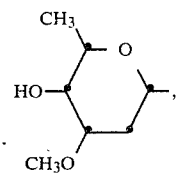

$R_2$ is —$CH_2CH_3$, and the 22, 23 bond is a double bond; in Compound II, $R_1$ is —H, $R_2$ is —$CH_2CH_3$, and the 22, 23 bond is a single bond; in Compound III, $R_1$ is

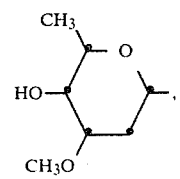

$R_2$ is —$CH_2CH_3$, and the 22, 23 bond is a single bond; in Compound IV, $R_1$ is —H, $R_2$ is —$CH_3$, and the 22, 23 bond is a single bond; or in Compound V, $R_1$ is

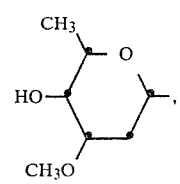

$R_2$ is —$CH_3$ and the 22, 23 bond is a single bond.

2. The compound of claim 1 which is Compound I wherein $R_1$ is

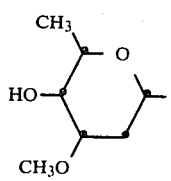

and R$_2$ is —CH$_2$CH$_3$ and the 22,23-bond is a double bond.

3. The compound of claim 1 which is Compound II wherein R$_1$ is hydrogen, R$_2$ is —CH$_2$CH$_3$ and the 22,23-bond is a single bond.

4. The compound of claim 1 which is Compound III wherein R$_1$ is

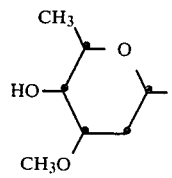

R$_2$ is —CH$_2$CH$_3$ and the 22,23-bond is a single bond.

5. The compound of claim 1 which is Compound IV wherein R$_1$ is hydrogen, R$_2$ is —CH$_3$ and the 22,23-position is a single bond.

6. The compound of claim 1 which is Compound V wherein R$_1$ is

R$_2$ is —CH$_3$ and the 22,23-bond is a single bond.

7. A composition useful as an antiparesitic agent which comprises an inert carrier and an effective amount of a compound of claim 1.

8. A method for the treatment of parasitic infections in a host which comprises treating the area of parasitic infection with an effective amount of a compound of claim 1.

* * * * *